United States Patent
Kim et al.

(10) Patent No.: US 11,978,857 B2
(45) Date of Patent: May 7, 2024

(54) NON-AQUEOUS ELECTROLYTE INCLUDING ADDITIVE FOR NON-AQUEOUS ELECTROLYTE, AND LITHIUM SECONDARY BATTERY INCLUDING THE NON-AQUEOUS ELECTROLYTE

(71) Applicant: LG Energy Solution, Ltd., Seoul (KR)

(72) Inventors: Hyung Tae Kim, Daejeon (KR); Chul Haeng Lee, Daejeon (KR); Jeong Woo Oh, Daejeon (KR); Byung Chun Park, Daejeon (KR); Young Mi Seo, Daejeon (KR); Sung Guk Park, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 0 days.

(21) Appl. No.: 17/956,064

(22) Filed: Sep. 29, 2022

(65) Prior Publication Data
US 2023/0101481 A1    Mar. 30, 2023

(30) Foreign Application Priority Data
Sep. 30, 2021  (KR) .................. 10-2021-0129871

(51) Int. Cl.
| | |
|---|---|
| *H01M 10/0568* | (2010.01) |
| *C07D 487/04* | (2006.01) |
| *H01M 10/052* | (2010.01) |
| *H01M 10/0567* | (2010.01) |
| *H01M 10/0569* | (2010.01) |

(52) U.S. Cl.
CPC ...... *H01M 10/0567* (2013.01); *C07D 487/04* (2013.01); *H01M 10/052* (2013.01); *H01M 10/0568* (2013.01); *H01M 10/0569* (2013.01); *H01M 2300/0037* (2013.01)

(58) Field of Classification Search
CPC ............ C07D 487/04; H01M 10/0567; H01M 10/052; H01M 10/0568; H01M 10/0569; H01M 2300/0037
See application file for complete search history.

(56) References Cited

U.S. PATENT DOCUMENTS

| | | | | |
|---|---|---|---|---|
| 2012/0171576 A1* | 7/2012 | Tsai | .................. | H01M 10/0567 429/207 |
| 2012/0171579 A1* | 7/2012 | Tsai | .................... | H01M 4/5815 429/207 |
| 2013/0004859 A1 | 1/2013 | Yu et al. | | |
| 2013/0078533 A1* | 3/2013 | Kang | ................ | H01M 10/0567 429/188 |

FOREIGN PATENT DOCUMENTS

| | | |
|---|---|---|
| JP | H09007895 A | 1/1997 |
| JP | H9139233 A | 5/1997 |
| JP | 2013045920 A | 3/2013 |
| JP | 2016006759 A | 1/2016 |
| JP | 2016192465 A | 11/2016 |
| KR | 20090080298 A | 7/2009 |
| KR | 20130003865 A | 1/2013 |
| KR | 20130032104 A | 4/2013 |

OTHER PUBLICATIONS

Morales-Collazo, "6,7-dihydro-5H-pyrrolo[1,2-a]imidazole" IUCrDATA, 2020, vol. 5, No. x200681, p. 1-3 (Year: 2020).*
Husch et al., Phys.Chem.Chem. Phys.,2015, 17, 22596 (Hush, Abstract (Year: 2015).*
Decision of KPO to grant a Patent (Year: 2023).*
Morales, O. et al., "6,7-Dihydro-5H-pyrrolo[1,2-a]imidazole" IUCrData, May 2020, ISSN 2414-3146, data reports, pp. 1-6. vol. 5. article No. X200681.
Gurav. S. et al., "Development and validation of an enantioselective LC-MS/MS method to quantify enantiomers of (±) -TAK-700 in rat plasma: lack of in vivo inversion of (+)-TAK-700 (Orteronel) to its antipode" Biomedical Chromatography, John Wiley & Sons, Ltd, Jun. 2012, pp. 1-8.
Weldon, M. S. et al., "Selectivity of BI 689648, a Novel, Highly Selective Aldosterone Synthase Inhibitor: Comparison with FAD286 and LCI699 in Nonhuman Primates" The American Society for Pharmacology and Expermiental Therapeutics, Oct. 2016, pp. 142-150, vol. 359, issue 1.

* cited by examiner

*Primary Examiner* — Alexander Usyatinsky
(74) *Attorney, Agent, or Firm* — Lerner David LLP

(57) ABSTRACT

The present disclosure provides a non-aqueous electrolyte including an additive for a non-aqueous electrolyte represented by Formula 1 below:

[Formula 1]

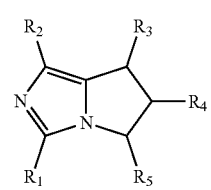

wherein, $R_1$ to $R_5$ may each independently be any one selected from the group consisting of H, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, and a nitrile group.

13 Claims, No Drawings

NON-AQUEOUS ELECTROLYTE INCLUDING ADDITIVE FOR NON-AQUEOUS ELECTROLYTE, AND LITHIUM SECONDARY BATTERY INCLUDING THE NON-AQUEOUS ELECTROLYTE

CROSS-REFERENCE TO RELATED APPLICATIONS

This application claims the priority from Korean Patent Application No. 10-2021-0129871 filed on Sep. 30, 2021, the disclosure of which is incorporated herein by reference.

BACKGROUND OF THE INVENTION

The present disclosure relates to a non-aqueous electrolyte including an additive for a non-aqueous electrolyte, and a lithium secondary battery including the non-aqueous electrolyte.

Recently, as the application area of lithium secondary batteries has rapidly expanded to the power supply of electronic devices such as electricity, electronics, communications, and computers, as well as the power storage supply of large-area devices such as automobiles and power storage devices, the demand for high-capacity, high-output, and high-stability secondary batteries is increasing.

Particularly, in lithium secondary batteries for automotive applications, the properties of high capacity, high power, and long lifespan are becoming important. For the high capacity of a secondary battery, a positive electrode active material with a high content of nickel which is high in energy density but low in stability may be used, or the secondary battery may be driven at a high voltage.

However, when a secondary battery is driven under the above condition, as charge and discharge proceeds, a film formed on surfaces of positive/negative electrodes or the surface structure of an electrode is deteriorated by a side reaction caused by the deterioration of an electrolyte, so that transition metal ions may be eluted from the surface of the positive electrode. As described above, the eluted transition metal ions are electro-deposited on the negative electrode and cause the passivation capability of SEI to degrade, so that there is a problem in that the negative electrode is deteriorated.

The deterioration phenomenon of a secondary battery tends to accelerate when the potential of a positive electrode increases, or when the battery is exposed to high temperatures.

In addition, when a lithium ion battery is continuously used for a long period of time or left to stand at high temperatures, gas is generated and causes a so-called swelling phenomenon in which the thickness of the battery increases, and it is known that the amount of gas generated at this time depends on the state of the SEI.

Therefore, in order to solve the above problem, research and development are being conducted on methods capable of suppressing the elution of metal ions from a positive electrode and forming a stable SEI film on a negative electrode, thereby reducing the swelling phenomenon of a secondary battery, and increasing the stability at high temperatures.

BRIEF SUMMARY OF THE INVENTION

An aspect of the present disclosure provides an additive for a non-aqueous electrolyte capable of suppressing the degradation of a positive electrode, reducing side reactions between a positive electrode and an electrolyte, and forming a stable SEI film on a negative electrode.

Another aspect of present disclosure provides a non-aqueous electrolyte having improved stability at high temperatures by including the additive for a non-aqueous electrolyte.

Another aspect of the present disclosure provides a lithium secondary battery with improved overall performance by including the non-aqueous electrolyte, thereby having improved high-temperature cycle properties and high-temperature storage properties.

According to an aspect of the present disclosure, there is provided a non-aqueous electrolyte including an additive for a non-aqueous electrolyte represented by Formula 1 below.

[Formula 1]

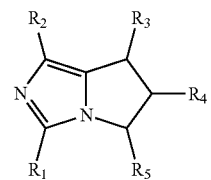

In Formula 1 above, $R_1$ to $R_5$ may each independently be anyone selected from the group consisting of H, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, and a nitrile group.

According to another aspect of the present disclosure, there is provided a lithium secondary battery including the non-aqueous electrolyte of the present disclosure.

A compound represented by Formula 1 above, which is provided as an additive for a non-aqueous electrolyte of the present disclosure, is a compound based on an imidazole structure in which a cycloalkyl ring is fused, and is capable of forming a stable solid electrolyte interphase (SEI) film on the surface of a negative electrode while minimizing an increase in the resistance of a lithium secondary battery. Therefore, it is possible to suppress the degradation in passivation capability of SEI at high temperatures, thereby preventing the negative electrode from deteriorating.

In addition, the compound represented by Formula 1 above, which is provided as the additive for a non-aqueous electrolyte of the present disclosure, has high binding energy with $PF_5$, which is a by-product of charging/discharging $LiPF_6$ used as a lithium salt, so that there is an effect of increasing battery durability by suppressing an additional decomposition reaction of $PF_5$.

Therefore, when the non-aqueous electrolyte of the present disclosure including the compound of Formula 1 above is used, it is possible to form an electrode-electrolyte interface which is stable at high temperatures and low in resistance, so that high-temperature cycle properties and high-temperature storage properties are improved to implement a lithium secondary battery with improved overall performance.

DETAILED DESCRIPTION OF THE INVENTION

It will be understood that terms or words used in the present specification and claims shall not be construed as being limited to having meanings defined in commonly used dictionaries, but should be interpreted as having meanings and concepts consistent with the technical idea of the present disclosure based on the principle that an inventor may appropriately define concepts of the terms to best explain the disclosure.

In the present specification, it should be understood that the terms "include," "comprise," or "have" are intended to specify the presence of stated features, numbers, steps, elements, or combinations thereof, but do not preclude the presence or addition of one or more other features, numbers, steps, elements, or combinations thereof.

In addition, in the present specification, it will be understood that in the description of "carbon atoms a to b" herein, "a" and "b" refer to the number of carbon atoms included in a specific functional group. That is, the functional group may include "a" to "b" number of carbon atoms. For example, an "alkylene group having 1 to 5 carbon atoms" refers to an alkylene group including carbon atoms with a carbon number of 1 to 5, that is, —$CH_2$—, —$CH_2CH_2$—, —$CH_2CH_2CH_2$—, —$CH_2CH$ ($CH_3$)—, —$CH(CH_3)CH_2$—, —$CH(CH_3)CH_2CH_2$—, and the like.

In addition, in the present disclosure, the term "alkylene group" refers to a branched or unbranched divalent unsaturated hydrocarbon group.

In addition, in the present specification, an alkyl group or an alkylene group may be substituted or unsubstituted. Unless otherwise defined, the term "substituted" means that at least one hydrogen bonded to carbon is substituted with an element other than hydrogen, and for example, it means being substituted with an alkyl group having 1 to 20 carbon atoms, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, a heterocycloalkyl group having 3 to 12 carbon atoms, a heterocycloalkenyl group having 3 to 12 carbon atoms, a heterocycloalkynyl group having 2 to 12 carbon atoms, an aryloxy group having 6 to 12 carbon atoms, a halogen atom, a fluoroalkyl group having 1 to 20 carbon atoms, a nitro group, an aryl group having 6 to 20 carbon atoms, a heteroaryl group having 2 to 20 carbon atoms, and a haloaryl group having 6 to 20 carbon atoms.

Hereinafter, the present disclosure will be described in more detail.

Non-Aqueous Electrolyte

A non-aqueous electrolyte according to an embodiment of the present disclosure includes a compound represented by Formula 1 below as an additive. A secondary battery including the non-aqueous electrolyte of the present disclosure may have excellent high-temperature cycle properties and high-temperature storage properties since deterioration caused by interfacial reactions at high temperatures are suppressed.

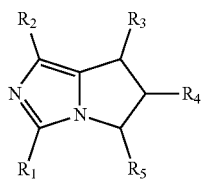

[Formula 1]

The compound of Formula 1 above is a compound based on an imidazole structure in which a cycloalkyl ring is fused, and is capable of forming a stable solid electrolyte interphase (SEI) film on the surface of a negative electrode while minimizing an increase in the resistance of a lithium secondary battery. Therefore, it is possible to suppress the degradation in passivation capability of SEI at high temperatures, thereby preventing the negative electrode from deteriorating.

In Formula 1 above, $R_1$ to $R_5$ may each independently be any one selected from the group consisting of H, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, and a nitrile group. Preferably, in Formula 1 above, $R_1$ and $R_2$ may be H, $R_3$ to $R_5$ may each independently be any one selected from the group consisting of H, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, and a nitrile group. Most preferably, $R_1$ to $R_5$ of Formula 1 above may be H.

An additive for a non-aqueous electrolyte according to the present disclosure may be included in an amount of 0.01 parts by weight to 5 parts by weight, preferably 0.05 parts by weight to 0.9 parts by weight, more preferably 0.1 parts by weight to 0.5 parts by weight, and most preferably 0.3 parts by weight, based on 100 parts by weight of the non-aqueous electrolyte. When the content of the compound represented by Formula 1 above satisfies the above range, there is a sufficient effect of forming a film on a positive electrode, thereby achieving an effect of suppressing the elution of a transition metal from a positive electrode active material, and the viscosity of the electrolyte is maintained at a suitable level, thereby achieving an effect in that rate properties or lifespan properties are excellent during high-temperature storage.

The non-aqueous electrolyte according to the present disclosure may further include a lithium salt, an organic solvent, or other electrolyte additives.

The lithium salt is used as an electrolyte salt in a lithium secondary battery, and is used as a medium for transferring ions. Typically, the lithium salt may include $Li^+$ as cations, and may include at least one selected from the group consisting of $F^-$, $Cl^-$, $Br^-$, $I^-$, $NO_3^-$, $N(CN)_2^-$, $BF_4^-$, $ClO_4^-$, $B_{10}Cl_{10}^-$, $AlCl_4^-$, $AlO_4^-$, $PF_6^-$, $CF_3SO_3^-$, $CH_3CO_2^-$, $CF_3CO_2^-$, $AsF_6^-$, $SbF_6^-$, $CH_3SO_3^-$, $(CF_3CF_2SO_2)_2N^-$, $(CF_3SO_2)_2N^-$, $(FSO_2)_2N^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $C_4F_9SO_3^-$, $CF_3CF_2SO_3^-$, $CF_3CF_3(CF_3)_2CO^-$, $(CF_3SO_2)_2CH^-$, $CF_3(CF_2)_7SO_3^-$, and $SCN^-$ as anions.

Specifically, the lithium salt may include a single material selected from the group consisting of LiCl, LiBr, LiI, $LiBF_4$, $LiClO_4$, $LiB_{10}Cl_{10}$, $LiAlCl_4$, $LiAlO_2$, $LiPF_6$, $LiCF_3SO_3$, $LiCH_3CO_2$, $LiCF_3CO_2$, $LiAsF_6$, $LiSbF_6$, $LiCH_3SO_3$, $LiN(SO_2F)_2$(lithium bis(fluorosulfonyl)imide (LiFSI)), $LiN(SO_2CF_2CF_3)_2$(lithium bis(perfluoroethanesulfonyl)imide (LiBETI)), and $LiN(SO_2CF_3)_2$(lithium bis(trifluoromethane)insulfonyl)imide (LiTFSI)), or a mixture of two or more thereof. In addition to the above, any lithium salt commonly used in an electrolyte of a lithium secondary battery may be used without limitation.

In order to obtain an optimum effect of forming an anti-corrosive film on the surface of an electrode, the lithium salt may be included in the electrolyte at a concentration of 0.5 M to 4 M, preferably 0.5 M to 3 M, more preferably 0.8 M to 2 M. When the concentration of the lithium salt satisfies the above range, there is a sufficient effect of improving cycle properties during high-temperature storage of a lithium secondary battery, and the viscosity of the non-aqueous electrolyte is suitable, so that the wettability of the electrolyte may be improved.

The non-aqueous electrolyte according to the present disclosure may include $LiPF_6$ as a lithium salt in terms of excellent high-temperature stability. In this case, the compound represented by Formula 1 above has high binding energy with $PF_5$, which is a by-product of charging/discharging $LiPF_6$ used as a lithium salt, so that there may be an effect of increasing battery durability by suppressing an additional decomposition reaction of $PF_5$.

In addition, in order to prepare an electrolyte having a high ion conductivity, the organic solvent may include at least one carbonate-based organic solvent selected from the group consisting of the cyclic carbonate-based organic solvent and the linear carbonate-based organic solvent and at least one ester-based organic solvent selected from the group consisting of the linear ester-based organic solvent and the cyclic ester-based organic solvent.

The non-aqueous organic solvent may include at least one organic solvent selected from the group consisting of a cyclic carbonate-based organic solvent, a linear carbonate-based organic solvent, a linear ester-based organic solvent, and a cyclic ester-based organic solvent.

Specifically, the organic solvent may include a cyclic carbonate-based organic solvent, a linear carbonate-based organic solvent, or a mixed organic solvent thereof.

The cyclic carbonate-based organic solvent is an organic solvent having high viscosity and a high dielectric constant, and thus, is an organic solvent capable of dissociating a lithium salt well in an electrolyte, and specific examples thereof may include at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and among them, may include ethylene carbonate.

In addition, the linear carbonate-based organic solvent is an organic solvent having low viscosity and a low dielectric constant, and representative examples thereof may include at least one organic solvent selected from the group consisting of dimethyl carbonate (DMC), diethyl carbonate (DEC), dipropyl carbonate, ethylmethyl carbonate (EMC), methylpropyl carbonate, and ethylpropyl carbonate, and specifically, may include ethylmethyl carbonate (EMC).

Specific examples of the linear ester-based organic solvent may include at least one organic solvent selected from the group consisting of methyl acetate, ethyl acetate, propyl acetate, methyl propionate, ethyl propionate, propyl propionate, and butyl propionate.

In addition, the cyclic ester-based organic solvent may be at least one organic solvent selected from the group consisting of γ-butyrolactone, γ-valerolactone, γ-caprolactone, σ-valerolactone, and ε-caprolactone.

Meanwhile, if necessary, the organic solvent may additionally use any organic solvent commonly used in a non-aqueous electrolyte without limitation. For example, the organic solvent may further include at least one organic solvent among an ether-based organic solvent, a glyme-based solvent, and a nitrile-based organic solvent.

As the ether-based solvent, any one selected from the group consisting of dimethyl ether, diethyl ether, dipropyl ether, methyl ethyl ether, methyl propyl ether, ethyl propyl ether, 1,3-dioxolane (DOL), and 2,2-bis (trifluoromethyl)-1,3-dioxolane (TFDOL), or a mixture of two or more thereof may be used, but the present disclosure is not limited thereto.

The glyme-based solvent is a solvent having a higher dielectric constant and lower surface tension than those of a linear carbonate-based organic solvent, and having less reactivity with a metal, and may include at least one selected from the group consisting of dimethoxyethane (glyme, DME), diethoxyethane, digylme, tri-glyme, and tetra-glyme (TEGDME), but is not limited thereto.

The nitrile-based solvent may be one or more selected from the group consisting of acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, but is not limited thereto.

In addition, the non-aqueous electrolyte of the present disclosure may further include, if necessary, an electrolyte additive known in the art in the non-aqueous electrolyte to prevent the non-aqueous electrolyte from being decomposed in a high-output environment and causing a negative electrode to collapse, or to further improve low-temperature high-rate discharge properties, high-temperature stability, overcharge prevention, the effect of suppressing battery expansion at high temperatures, and the like.

Representative examples of the electrolyte additive may include at least one additional additive that is not described above for forming an SEI film, and such additive may be selected from the group consisting of a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, and a lithium salt-based compound, which are not described above.

The cyclic carbonate-based compound may be vinylene carbonate (VC) or vinylethylene carbonate.

The halogen-substituted carbonate-based compound may be fluoroethylene carbonate (FEC).

The sultone-based compound may be at least one compound selected from the group consisting of 1,3-propane sultone (PS), 1,4-butane sultone, ethene sulfone, 1,3-propene sultone (PRS), 1,4-butene sultone, and 1-methyl-1,3-propene sultone.

The sulfate-based compound may be ethylene sulfate (ESA), trimethylene sulfate (TMS) or methyl trimethylene sulfate (MTMS).

The phosphate-based compound may be one or more compound selected from lithium difluoro(bisoxalato)phosphate, lithium difluorophosphate, tetramethyl trimethyl silyl phosphate, trimethyl silyl phosphite, tris(2,2,2-trifluoroethyl)phosphate, or tris(trifluoroethyl)phosphite.

The borate-based compound may be tetraphenylborate, lithium oxalyldifluoroborate (LiODFB), or lithium bisoxalatoborate ($LiB(C_2O_4)_2$, LiBOB).

The nitrile-based compound may be at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The benzene-based compound may be fluorobenzene, the amine-based compound may be triethanolamine, ethylene diamine, or the like, and the silane-based compound may be tetravinylsilane.

The lithium salt-based compound is a compound different from the lithium salt included in the non-aqueous electrolyte, and may be lithium difluorophosphate (LiDFP), $LiPO_2F_2$, $LiBF_4$, or the like.

Among the electrolyte additives, when a combination of vinylene carbonate (VC), 1,3-propane sultone (PS), ethylene sulfate (Esa), and lithium difluorophosphate (LiDFP) is included, it is possible to form a more robust SEI film on the surface of a negative electrode during an initial activation process of a secondary battery, and to suppress the generation of a gas which may be generated due to the decomposition of an electrolyte at high temperatures, thereby improving high-temperature stability of the secondary battery.

Meanwhile, two or more of the electrolyte additives may be mixed and used, and may be 0.05 to 20 wt %, specifically 0.1 to 15 wt %, preferably 0.3 to 10 wt %, based on the total weight of the non-aqueous electrolyte. When the content of the electrolyte additives satisfies the above range, there is a more excellent effect of improving ion conductivity and cycle properties.

Lithium Secondary Battery

The present disclosure also provides a lithium secondary battery including the non-aqueous electrolyte.

Specifically, the lithium secondary battery includes a positive electrode including a positive electrode active material, a negative electrode including a negative electrode active material, a separator interposed between the positive electrode and the negative electrode, and the above-described non-aqueous electrolyte.

At this time, the lithium secondary battery of the present disclosure may be manufactured by a typical method known in the art. For example, the lithium secondary battery of the present disclosure may be manufactured by forming an electrode assembly in which a positive electrode, a negative electrode, and a separator between the positive electrode and the negative electrode are sequentially stacked, followed by inserting the electrode assembly in a battery case, and then injecting the non-aqueous electrolyte according to the present disclosure thereto.

(1) Positive Electrode

The positive electrode may be manufactured by coating a positive electrode mixture slurry including a positive electrode active material, a binder, a conductive material, a solvent, and the like on a positive electrode current collector.

The positive electrode current collector is not particularly limited as long as it has conductivity without causing a chemical change in the battery. For example, stainless steel, aluminum, nickel, titanium, fired carbon, or aluminum or stainless steel that is surface-treated with one of carbon, nickel, titanium, silver, and the like may be used.

The positive electrode active material is a compound capable of reversible intercalation and de-intercalation of lithium, and specifically, may include a lithium metal oxide including one or more metals such as cobalt, manganese, nickel, or aluminum, and lithium. More specifically, the lithium metal oxide may be a lithium-manganese-based oxide (e.g., $LiMnO_2$, $LiMn_2O_4$, etc.), a lithium-cobalt-based oxide (e.g., $LiCoO_2$, etc.), a lithium-nickel-based oxide (e.g., $LiNiO_2$, etc.), a lithium-nickel-manganese-based oxide (e.g., $LiNi_{1-Y}Mn_YO_2$ (wherein 0<Y<1), $LiMn_{2-Z}Ni_ZO_4$ (wherein 0<Z<2, etc.), a lithium-nickel-cobalt-based oxide (e.g., $LiNi_{1-Y1}Co_{Y1}O_2$ (wherein 0<Y1<1, etc.), a lithium-manganese-cobalt-based oxide (e.g., $LiCo_{1-Y2}Mn_{Y2}O_2$ (wherein 0<Y2<1), $LiMn_{2-Z1}Co_{Z1}O_4$ (wherein 0<Z1<2, etc.), a lithium-nickel-manganese-cobalt-based oxide (e.g., $Li(Ni_pCo_qMn_r)O_2$ (wherein 0<p<1, 0<q<1, 0<r<1, and p+q+r=1) or $Li(Ni_{p1}Co_{q1}Mn_{r1})O_4$ (wherein 0<p1<2, 0<q1<2, 0<r1<2, and p1+q1+r1=2, etc.), or a lithium-nickel-cobalt-transition metal (M) oxide (e.g., $Li(Ni_{p2}Co_{q2}Mn_{r2}M_{s2})O_2$ (wherein M is selected from the group consisting of Al, Fe, V, Cr, Ti, Ta, Mg, and Mo, and p2, q2, r2, and s2 are each an atomic fraction of stand-alone elements, wherein 0<p2<1, 0<q2<1, 0<r2<1, 0<s2<1, and p2+q2+r2+s2=1), etc.) and the like, and any one thereof or a compound of two or more thereof may be included.

Among these, due to the fact that the capacity properties and stability of a battery may be increased, the lithium metal oxide may be $LiCoO_2$, $LiMnO_2$, $LiNiO_2$, a lithium nickel-manganese-cobalt oxide (e.g., $Li(Ni_{1/3}Mn_{1/3}Co_{1/3})O_2$, $Li(Ni_{0.6}Mn_{0.2}Co_{0.2})O_2$, $Li(Ni0.5Mn0.3Co_{0.2})O_2$, $Li(Ni0.7Mn_{0.15}Co_{0.15})O_2$, $Li(Ni_{0.8}Mn_{0.1}Co_{0.1})O_2$, etc.), a lithium nickel cobalt aluminum oxide (e.g., $Li(Ni0.8Co0.15Al_{0.05})O_2$, etc.), or the like, and any one thereof or a mixture of two or more thereof may be used.

Among the above, a positive electrode active material having a nickel content of 80 atm % or greater may be used in that capacity properties of a battery may be most increased. For example, the lithium transition metal oxide may include one represented by [Formula 2] below.

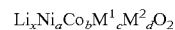

$$Li_xNi_aCo_bM^1_cM^2_dO_2 \qquad \text{[Formula 2]}$$

In Formula 2 above, $M^1$ is one or more selected from Mn and Al, and preferably, may be Mn or a combination of Mn and Al.

$M^2$ is one or more selected from the group consisting of Zr, B, W, Mg, Ce, Hf, Ta, La, Ti, Sr, Ba, F, P, and S.

The x represents an atomic fraction of lithium in a lithium transition metal oxide, wherein the x may satisfy 0.90≤x≤1.1, preferably 0.95≤x≤1.08, more preferably 1.0≤x≤1.08.

The a represents an atomic fraction of nickel among metal elements excluding lithium in a lithium transition metal oxide, wherein the a may satisfy 0.80≤a<1.0, preferably 0.80≤a≤0.95, more preferably 0.80≤a≤0.90. When the nickel content satisfies the above range, it is possible to implement high-capacity properties.

The b represents an atomic fraction of cobalt among metal elements excluding lithium in a lithium transition metal oxide, wherein the b may satisfy 0<b<0.2, 0<b≤0.15, or 0.01≤b≤0.10.

The c represents an atomic fraction of $M^1$ among metal elements excluding lithium in a lithium transition metal oxide, wherein the c may satisfy 0<c<0.2, 0<c≤0.15, or 0.01≤c≤0.10.

The d represents an atomic fraction of $M^2$ among metal elements excluding lithium in a lithium transition metal oxide, wherein the d may satisfy 0≤d≤0.1, or 0≤d≤0.05.

The positive electrode active material may be included in an amount of 60 wt % to 99 wt %, preferably 70 wt % to 99 wt %, more preferably 80 wt % to 98 wt %, based on the total weight of solids excluding the solvent in the positive electrode mixture slurry.

The binder is a component for assisting in coupling between an active material and a conductive material, and coupling to a current collector.

Examples of the binder may include polyvinylidene fluoride, polyvinyl alcohol, starch, hydroxypropyl cellulose, regenerated cellulose, polyvinylpyrrolidone, polytetrafluoroethylene, polyethylene (PE), polypropylene, an ethylene-propylene-diene monomer, a sulfonated ethylene-propylene-diene monomer, styrene-butadiene rubber, fluorine rubber, and various copolymers thereof.

Typically, the binder may be included in an amount of 1 to 20 wt %, preferably 1 to 15 wt %, more preferably 1 wt % to 10 wt %, based on the total weight of solids excluding the solvent in the positive electrode mixture slurry.

The conductive material is a component for further improving the conductivity of the positive electrode active material, and may be added in an amount of 1 to 20 wt % based on the total weight of solids in the positive electrode mixture slurry. The conductive material is not particularly limited as long as it has conductivity without causing a chemical change in the battery, and for example, carbon powder such as carbon black, acetylene black, Ketjen black, channel black, furnace black, lamp black, or thermal black; graphite powder of natural graphite, artificial graphite, graphite, or the like, which has a very developed crystal structure; conductive fiber such as carbon fiber or metal fiber; conductive powder such as fluorocarbon powder, aluminum powder, and nickel powder; a conductive whisker such as zinc oxide and potassium titanate; a conductive metal oxide such as titanium oxide; a conductive material such as a polyphenylene derivative, and the like may be used.

Typically, the binder may be included in an amount of 1 to 20 wt %, preferably 1 to 15 wt %, more preferably 1 wt % to 10 wt %, based on the total weight of solids excluding the solvent in the positive electrode mixture slurry.

The solvent may include an organic solvent such as N-methyl-2-pyrrolidone (NMP), and may be used in an amount such that a preferred viscosity is achieved when the positive electrode active material, and selectively, a binder, a conductive material, and the like are included. For example, the solvent may be included in an amount such that the concentration of a solid including the positive electrode active material, and selectively the binder and the conductive material is 50 wt % to 95 wt %, preferably 70 wt % to 95 wt %, more preferably 70 wt % to 90 wt %.

(2) Negative Electrode

The negative electrode may be manufactured by, for example, coating a negative electrode mixture slurry containing a negative electrode active material, a binder, a conductive material, a solvent, and the like on a negative electrode current collector, or a graphite electrode made of carbon (C) or a metal itself may be used as the negative electrode.

For example, when the negative electrode is manufactured by coating a negative electrode mixture slurry on a negative electrode current collector, the negative electrode current collector typically has a thickness of 3 to 500 μm. The negative electrode current collector is not particularly limited as long as it has high conductivity without causing a chemical change in the battery, and for example, copper, stainless steel, aluminum, nickel, titanium, fired carbon, copper or stainless steel that is surface-treated with one of carbon, nickel, titanium, silver, and the like, an aluminum-cadmium alloy, and the like may be used. Also, as in the case of the positive electrode current collector, microscopic irregularities may be formed on the surface of the negative electrode current collector to improve the binding force of a negative electrode active material, and the negative electrode current collector may be used in various forms of such as a film, a sheet, a foil, a net, a porous body, a foam body, and a non-woven fabric body.

In addition, the negative electrode active material may include at least one selected from the group consisting of a lithium metal, a carbon material capable of reversible intercalation/de-intercalation of lithium ions, a metal or an alloy of the metal and lithium, a metal composite oxide, a material capable of doping and undoping lithium, and a transition metal oxide.

As the carbon material capable of reversible intercalation/de-intercalation of lithium ions, a carbon-based negative electrode active material commonly used in a lithium ion secondary battery may be used without particular limitation, and representative examples thereof may include a crystalline carbon, an amorphous carbon, or a combination thereof. Examples of the crystalline carbon may include graphite such as an irregular, planar, flaky, spherical, or fibrous natural graphite or artificial graphite, and examples of the amorphous carbon may include soft carbon (low-temperature fired carbon) or hard carbon, mezophase pitch carbides, fired cokes, and the like.

As the metal or the alloy of the metal and lithium, a metal selected from the group consisting of Cu, Ni, Na, K, Rb, Cs, Fr, Be, Mg, Ca, Sr, Si, Sb, Pb, In, Zn, Ba, Ra, Ge, Al, and Sn, or an alloy of the metal and lithium may be used.

As the metal composite oxide, one selected from the group consisting of $PbO$, $PbO_2$, $Pb_2O_3$, $Pb_3O_4$, $Sb_2O_3$, $Sb_2O_4$, $Sb_2O_5$, $GeO$, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_z$ (Me: Mn, Fe, Pb, Ge; Me': Al, B, P, Si, elements in Group 1, Group 2, and Group 3 of the periodic table, halogen; $0 < x \leq 1$; $1 \leq y \leq 3$; $1 \leq z \leq 8$) may be used.

The material capable of doping and undoping lithium may be Si, $SiO_x$ ($0 < x \leq 2$), an Si—Y alloy (wherein Y is an element selected from the group consisting of an alkali metal, an alkaline earth metal, a Group 13 element, a Group 14 element, a transition metal, a rare earth element, and a combination thereof, but not Si), Sn, $SnO_2$, Sn—Y (wherein Y is an element selected from the group consisting of an alkali metal, an alkaline earth metal, a Group 13 element, a Group 14 element, a transition metal, a rare earth element, and a combination thereof, but not Sn), and the like, or at least one thereof may be mixed with $SiO_2$ and used. The element Y may be selected from the group consisting of Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ge, P, As, Sb, Bi, S, Se, Te, Po, and a combination thereof.

The transition metal oxide may be a lithium-containing titanium composite oxide (LTO), a vanadium oxide, a lithium vanadium oxide, and the like.

The negative electrode active material may be included in an amount of 60 to 99 wt %, preferably 70 to 99 wt %, more preferably 80 to 98 wt %, based on the total weight of solids in the negative electrode mixture slurry.

The binder is a component for assisting in coupling between a conductive material, an active material, and a current collector. Examples of the binder may include polyvinylidene fluoride (PVDF), polyvinyl alcohol, starch, hydroxypropyl cellulose, regenerated cellulose, polyvinylpyrrolidone, polytetrafluoroethylene, polyethylene, polypropylene, an ethylene-propylene-diene monomer, a sulfonated ethylene-propylene-diene monomer, styrene-butadiene rubber, fluorine rubber, and various copolymers thereof. Specifically, styrene butadien rubber (SBR)-carboxylmethyl cellulose (CMC) may be used in terms of high thickening properties.

Typically, the binder may be included in an amount of 1 to 20 wt %, preferably 1 to 15 wt %, more preferably 1 wt % to 10 wt %, based on the total weight of solids excluding the solvent in the negative electrode mixture slurry.

The conductive material is a component for further improving the conductivity of the negative electrode active material, and may be added in an amount of 1 to 20 wt % based on the total weight of solids in the negative electrode mixture slurry. The conductive material is not particularly limited as long as it has conductivity without causing a chemical change in the battery, and for example, carbon powder such as carbon black, acetylene black, Ketjen black, channel black, furnace black, lamp black, or thermal black; graphite powder of natural graphite, artificial graphite, graphite, or the like, which has a very developed crystal structure; conductive fiber such as carbon fiber or metal fiber; conductive powder such as fluorocarbon powder, aluminum powder, and nickel powder; a conductive whisker such as zinc oxide and potassium titanate; a conductive metal oxide such as titanium oxide; a conductive material such as a polyphenylene derivative, and the like may be used.

The conductive material may be included in an amount of 1 to 20 wt %, preferably 1 to 15 wt %, more preferably 1 to 10 wt %, based on the total weight of solids excluding the solvent in the negative electrode mixture slurry.

The solvent may include an organic solvent such as water, or an organic solvent such as N-methyl-2-pyrrolidone (NMP), and may be used in an amount such that a preferred viscosity is achieved when the negative electrode active material, and selectively, a binder and a conductive material, and the like are included. For example, the solvent may be included in an amount such that the concentration of solids including the negative electrode active material, and selectively, a binder and a conductive material, is 50 wt % to 95 wt %, preferably 50 wt % to 95 wt %, preferably 70 wt % to 90 wt %.

As the negative electrode, when a metal itself is used, the negative electrode may be manufactured by physically bonding, roll-pressing, or depositing a metal on a metal thin film itself or the negative electrode current collector. The depositing method may be electrical vapor deposition or chemical vapor deposition.

For example, the metal bonded/roll-pressed/deposited on the metal thin film itself or the negative electrode current collector may be one type of metal selected from the group consisting of lithium (Li), nickel (Ni), tin (Sn), copper (Cu), and indium (In), or an alloy of two types of metals thereof.

(3) Separator

In addition, as the separator, a common porous polymer film typically used as a separator, for example, a porous polymer film prepared with a polyolefin-based polymer, such as an ethylene homocopolymer, a propylene homocopolymer, an ethylene/butene copolymer, an ethylene/hexene copolymer, and an ethylene/methacrylate copolymer may be used alone, or in a laminated form thereof. Alternatively, a typical porous non-woven fabric, for example, a non-woven fabric formed of a glass fiber having a high melting point or polyethylene terephthalate fiber may be used, but the present invention is not limited thereto. Also, a coated separator including a ceramic component or a polymer material may be used to secure heat resistance or mechanical strength, and may be selectively used in a single-layered or a multi-layered structure.

Specifically, separators included in an electrode assembly of the present disclosure may be a safety reinforced separator (SRS) in which a coating layer containing a ceramic component or a polymer material is formed to secure heat resistance or mechanical strength.

Specifically, the separators included in the electrode assembly of the present disclosure include a porous separator substrate, and a porous coating layer entirely coated on one surface or both surfaces of the separator substrate, wherein the coating layer may include a mixture of inorganic particles selected from a metal oxide, a metalloid oxide, a metal fluoride, a metal hydroxide, and a combination thereof, and a binder polymer for connecting and fixing the inorganic particles to each other.

The coating layer may include, as the inorganic particles, one or more selected from $Al_2O_3$, $SiO_2$, $TiO_2$, $SnO_2$, $CeO_2$, MgO, NiO, CaO, ZnO, $ZrO_2$, $Y_2O_3$, $SrTiO_3$, $BaTiO_3$, $Mg(OH)_2$, and MgF. Here, the inorganic particles may improve thermal stability of the separator. That is, the inorganic particles may prevent the separator from shrinking at high temperatures. In addition, the binder polymer may improve mechanical stability of the separator by fixing the inorganic particles.

The external shape of the lithium secondary battery of the present disclosure is not particularly limited, but may be a cylindrical shape using a can, a square shape, a pouch shape, a coin shape, or the like.

Hereinafter, the present disclosure will be described in more detail with reference to specific examples. However, the following examples are for illustrative purposes only to facilitate the understanding of the present disclosure, and does not limit the scope of the present disclosure. It will be apparent to those skilled in the art that various changes and modifications can be made without departing from the scope and spirit of the invention, and it is obvious that such variations and modifications are within the scope of the appended claims.

EXAMPLES

Example 1

(Preparation of Non-Aqueous Electrolyte)

A non-aqueous solution was prepared by dissolving $LiPF_6$ to 1.0 M, and vinylene carbonate (VC) to 0.5 wt % in an organic solvent (ethylene carbonate (EC):ethylmethyl carbonate (EMC)=30:70 volume ratio), and to the non-aqueous solution, 0.1 g of a compound of Formula 1-1 below was introduced to prepare a non-aqueous electrolyte.

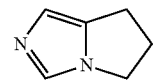

[Formula 1-1]

(Manufacturing of Lithium Secondary Battery)

A positive electrode active material ($LiNi_{0.9}Co_{0.06}Mn_{0.03}Al_{0.01}O_2$), a conductive material (carbon black) and a binder (polyvinylidene fluoride) were added in a weight ratio of 97.6:0.8:1.6 to N-methyl-2-pyrrolidone (NMP), which was a solvent, to prepare a positive electrode slurry (solid content 60 wt %). The positive electrode slurry was applied on one surface of a positive electrode current collector (Al thin film) having a thickness of 13.5 μm, dried and then roll-pressed to manufacture a positive electrode.

A negative electrode active material (graphite:SiO=90.0:10.0 weight ratio), a conductive material (carbon black) and a binder (styrene-butadiene rubber (SBR) -carboxylmethyl cellulose (CMC)) were added in a weight ratio of 97.6:0.8:

1.6 to N-methyl-2-pyrrolidone (NMP), which was a solvent, to prepare a negative electrode slurry (solid content 60 wt %). The negative electrode slurry was applied on one surface of a negative electrode current collector (Cu thin film) having a thickness of 6 μm, dried and then roll-pressed to manufacture a negative electrode.

In a dry room, a polyolefin-based porous separator on which inorganic particles $Al_2O_3$ were applied was interposed between the positive electrode and the negative electrode manufactured above, and then the prepared non-aqueous electrolyte was injected thereto to manufacture a secondary battery.

Example 2

A secondary battery was manufactured in the same manner as in Example 1 except that 0.3 g of the compound of Formula 1-1 above was introduced to 99.7 g of the non-aqueous solvent prepared in Example 1 to prepare a non-aqueous electrolyte.

Example 3

A secondary battery was manufactured in the same manner as in Example 1 except that 0.5 g of the compound of Formula 1-1 above was introduced to 99.5 g of the non-aqueous solvent prepared in Example 1 to prepare a non-aqueous electrolyte.

Comparative Example 1

A secondary battery was manufactured in the same manner as in Example 1 except that 100 g of the non-aqueous solution prepared in Example 1 was used to prepare a non-aqueous electrolyte.

Experimental Example 1—Evaluation of High-Temperature Cycle Properties

For each of the secondary batteries manufactured in Examples 1 to 3 and Comparative Example 1, cycle properties were evaluated.

Specifically, each of the batteries manufactured in Examples 1 to 3 and Comparative Example 1 was charged to 4.2 V with a constant current of 0.33 C at 45° C., and then discharged to 2.8 V with a constant current of 0.33 C, which was set to one cycle, and then 100 cycles of the charging/discharging were performed to measure a resistance increase rate after 100 cycles based on an initial resistance was measured. The results are shown in Table 1 below.

TABLE 1

|  | Resistance increase rate (%) |
| --- | --- |
| Example 1 | 6.37 |
| Example 2 | 4.72 |
| Example 3 | 6.25 |
| Comparative Example 1 | 8.58 |

As shown in Table 1, Examples 1 to 3 in which the additive for a non-aqueous electrolyte of the present disclosure was used had a lower resistance increase rate than that of Comparative Example 1 in which the additive was not used, and thus, had excellent lifespan properties.

Experimental Example 2—Evaluation of High-Temperature Storage Properties

For each of the secondary batteries manufactured in Examples 1 to 3 and Comparative Example 1, high-temperature storage properties were evaluated.

Specifically, the secondary batteries of Examples 1 to 3 and Comparative Example 1 were each fully charged to 4.2 V, and then stored at 60° C. for 4 weeks.

Before the storage, the volume of a body portion of each of the fully-charged secondary batteries was measured and then set to an initial volume of the secondary battery.

After 4 weeks, the volume of the body portion of each of the stored batteries was measured to calculate a volume increased during the 4-week storage period. The percentage ratio of the increased volume to the initial volume of the secondary battery was calculated to derive a volume increase rate after 4 weeks. The results are shown in Table 2 below.

TABLE 2

|  | Volume increase rate (%) |
| --- | --- |
| Example 1 | 15.72 |
| Example 2 | 13.58 |
| Example 3 | 14.27 |
| Comparative Example 1 | 16.41 |

As shown in Table 2 above, the secondary batteries of Examples 1 to 3 had a lower volume increase rate after 4 weeks than that of the secondary battery of Comparative Example 1, and thus, had less gas generation at high temperatures.

What is claimed is:

1. A non-aqueous electrolyte comprising an additive represented by Formula 1:

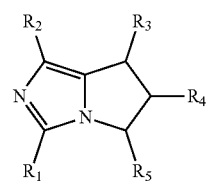

[Formula I]

wherein in Formula 1, $R_1$ to $R_5$ are each,
wherein the additive is included in a content of 0.01 parts by weight to 5 parts by weight based on 100 parts by weight of the non-aqueous electrolyte.

2. The non-aqueous electrolyte of claim 1, further comprising a lithium salt selected from LiCl, LiBr, LiI, $LiBF_4$, $LiClO_4$, $LiB_{10}Cl_{10}$, $LiAlCl_4$, $LiAlO_2$, $LiPF_6$, $LiCF_3SO_3$, $LiCH_3CO_2$, $LiCF_3CO_2$, $LiAsF_6$, $LiSbF_6$, $LiCH_3SO_3$, $LiN(SO_2F)_2$, $LiN(SO_2CF_2CF_3)_2$, $LiN(SO_2CF_3)_2$, or a combination thereof.

3. The non-aqueous electrolyte of claim 2, wherein the lithium salt is $LiPF_6$.

4. The non-aqueous electrolyte of claim 3, wherein the $LiPF_6$ is included at a concentration of 0.5 M to 4 M.

5. The non-aqueous electrolyte of claim 1, further comprising an organic solvent.

6. The non-aqueous electrolyte of claim 5, wherein the organic solvent comprises at least one of a cyclic carbonate organic solvent, a linear carbonate organic solvent, a linear ester organic solvent, or a cyclic ester organic solvent.

7. The non-aqueous electrolyte of claim 6, wherein the cyclic carbonate organic solvent comprises at least one of ethylene carbonate (EC), propylene carbonate (PC), 1,2-butylene carbonate, 2,3-butylene carbonate, 1,2-pentylene carbonate, 2,3-pentylene carbonate, or vinylene carbonate.

8. The non-aqueous electrolyte of claim 6, wherein the linear carbonate organic solvent comprises at least one of dimethyl carbonate (DMC), diethyl carbonate (DEC), dipropyl carbonate, ethylmethyl carbonate (EMC), methylpropyl carbonate, or ethylpropyl carbonate.

9. The non-aqueous electrolyte of claim 6, wherein the linear ester-organic solvent comprises at least one of methyl acetate, ethyl acetate, propyl acetate, methyl propionate, ethyl propionate, propyl propionate, or butyl propionate.

10. The non-aqueous electrolyte of claim 6, wherein the cyclic ester-organic solvent comprises at least one of γ-butyrolactone, γ-valerolactone, γ-caprolactone, σ-valerolactone, or ε-caprolactone.

11. The non-aqueous electrolyte of claim 5, wherein the organic solvent comprises a cyclic carbonate organic solvent, a linear carbonate organic solvent, or a combination thereof.

12. The non-aqueous electrolyte of claim 1, further comprising one or more of a cyclic carbonate compound, a halogen-substituted carbonate compound, a sultone compound, a sulfate compound, a phosphate compound, a borate compound, a nitrile compound, a benzene compound, an amine compound, a silane compound, or a lithium salt compound as an additive.

13. A lithium secondary battery comprising a positive electrode comprising a positive electrode active material, a negative electrode comprising a negative electrode active material, a separator interposed between the positive electrode and the negative electrode, and the non-aqueous electrolyte of claim 1.

* * * * *